(12) United States Patent
Wonnacott et al.

(10) Patent No.: US 10,517,979 B2
(45) Date of Patent: Dec. 31, 2019

(54) FRAGRANCE DISPENSER

(71) Applicant: Vectair Systems Limited, Basingstoke, Hampshire (GB)

(72) Inventors: Paul Wonnacott, Esher (GB); Matthew Teeling, Aldermaston (GB)

(73) Assignee: Vectair Systems Limited, Basingstoke, Hampshire (GB)

( * ) Notice: Subject to any disclaimer, the term of this patent is extended or adjusted under 35 U.S.C. 154(b) by 180 days.

(21) Appl. No.: 15/035,259

(22) PCT Filed: Oct. 28, 2014

(86) PCT No.: PCT/EP2014/073127
§ 371 (c)(1),
(2) Date: May 9, 2016

(87) PCT Pub. No.: WO2015/067505
PCT Pub. Date: May 14, 2015

(65) Prior Publication Data
US 2016/0279279 A1    Sep. 29, 2016

(30) Foreign Application Priority Data

Nov. 11, 2013    (GB) .................................. 1319889.0

(51) Int. Cl.
*A61L 9/12* (2006.01)
*A61L 9/04* (2006.01)

(52) U.S. Cl.
CPC ............... *A61L 9/125* (2013.01); *A61L 9/048* (2013.01); *A61L 2209/133* (2013.01)

(58) Field of Classification Search
CPC .................................. A61L 9/048; A61L 9/125
See application file for complete search history.

(56) References Cited

U.S. PATENT DOCUMENTS 5,527,493 A * 6/1996 McElfresh ........... B60H 3/0007
239/57
5,891,400 A 4/1999 Ansari
(Continued)

FOREIGN PATENT DOCUMENTS

EP    1076014    2/2001

OTHER PUBLICATIONS

European Patent Office, International Search Report, International Application No. PCT/EP2014/073127, 3 pages, dated Feb. 23, 2015.

*Primary Examiner* — Kevin Joyner
(74) *Attorney, Agent, or Firm* — Sunstein Kann Murphy & Timbers LLP

(57) ABSTRACT

A fragrance dispenser comprises a ceramic outer shell containing a gel composition. The ceramic can be greenware, and can be impregnated with a fragrance, such as in the form of a volatile oil. The gel composition can contain fragrance or deodourisers that can diffuse out of the gel and infuse the surrounding ceramic, from which it can be released into the air. The ceramic cartridge can have indentations to allow it to be retained in a desired location; these can permit the attachment of a plastic mounting clip having a plurality of flexible arms that slot into the indentations to grip and hold the cartridge in place. This mounting clip could then be used to attach the cartridge to suitable surfaces such as a bathroom wall or the interior of a dispenser housing. Furthermore, the cartridge can have a locating recess on one or more of its sides, to receive a mounting post and thereby position the dispenser accurately and inhibit dislodgement.

19 Claims, 6 Drawing Sheets

(56) References Cited

U.S. PATENT DOCUMENTS

| | | |
|---|---|---|
| 6,085,026 A | 7/2000 | Hammons et al. |
| 6,425,530 B1 * | 7/2002 | Coakley .................... A61L 9/04 |
| | | 239/52 |
| 6,610,254 B1 * | 8/2003 | Furner ................ A01M 1/2033 |
| | | 222/183 |
| 11,079,658 | 4/2011 | Santini et al. |
| 2008/0156896 A1 * | 7/2008 | Anderson ............ B65D 83/262 |
| | | 239/34 |
| 2010/0221144 A1 * | 9/2010 | Bedson .................... A61L 9/12 |
| | | 422/4 |

\* cited by examiner

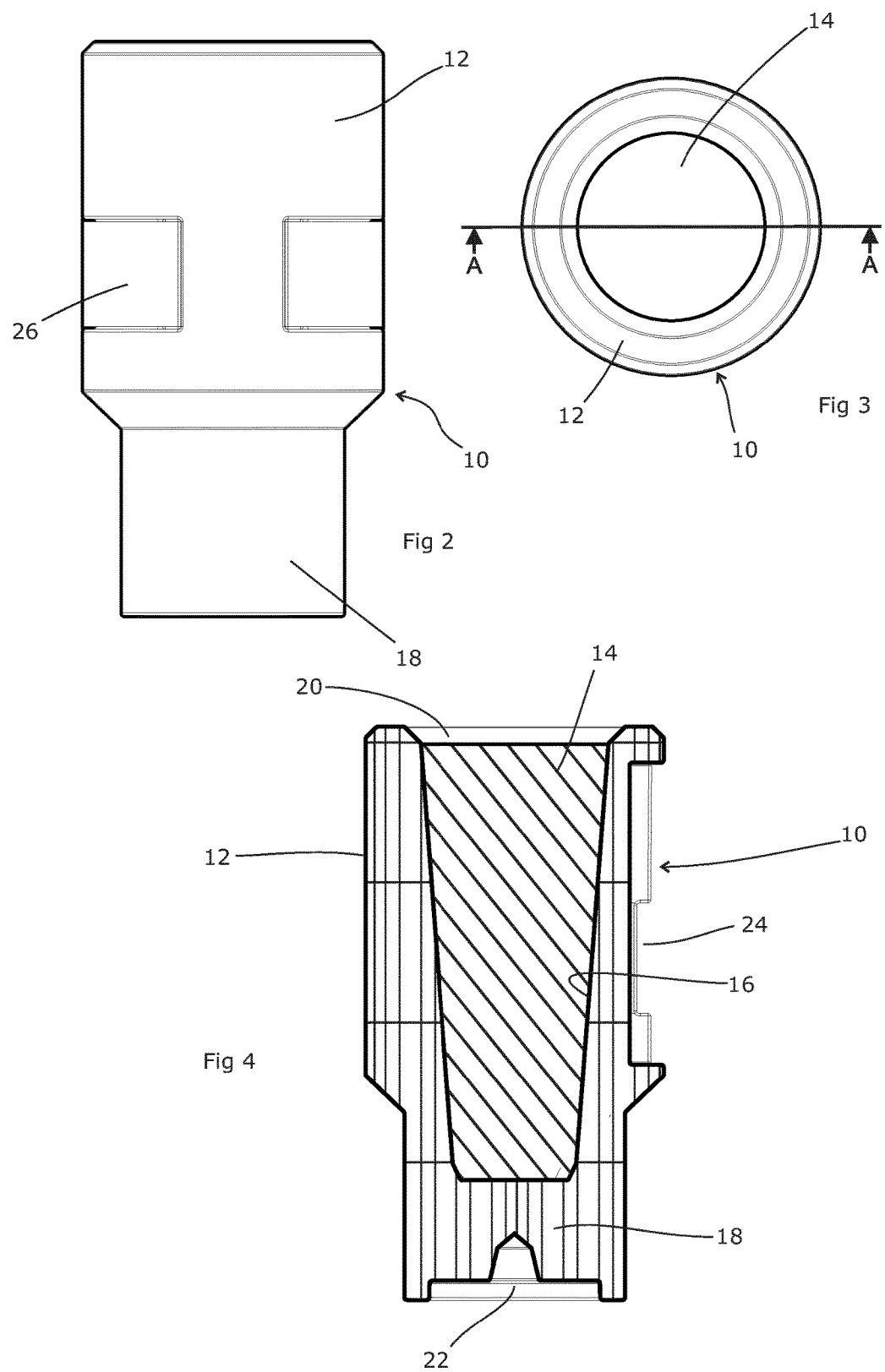

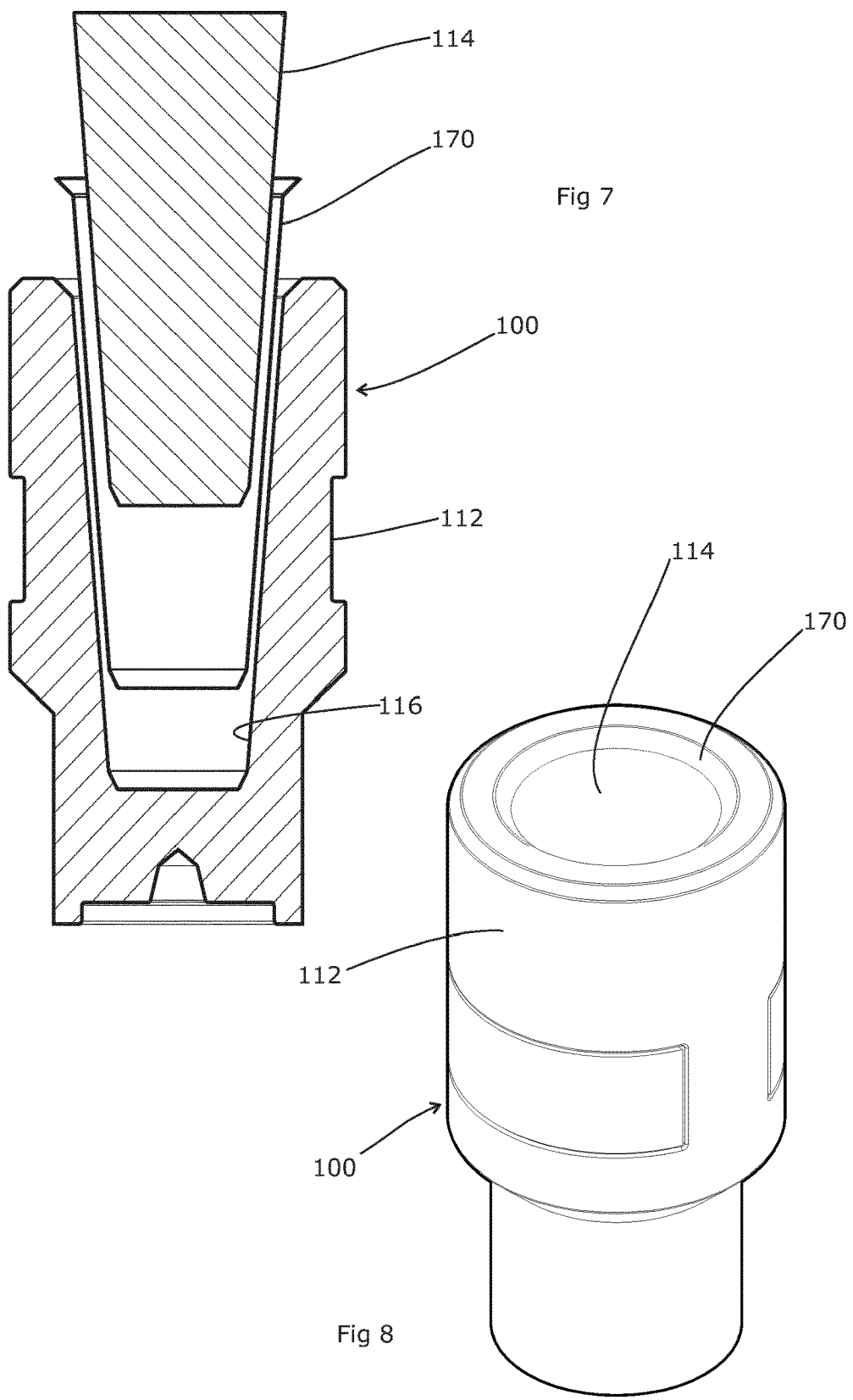

FRAGRANCE DISPENSER

FIELD OF THE INVENTION

The present invention relates to fragrance dispensers.

BACKGROUND ART

Fragrance dispensers are used to add, remove or mask odours through the release of one or more aromatic compounds (i.e. compounds with an agreeable aroma) or through the use of compounds that absorb or neutralise odours. In addition, the compounds that are released can include, or consist of, compounds having an insect repellent property. For convenience, we will refer to all three types of compounds as "fragrance".

Long-lasting fragrance dispensers primarily consist of a housing within which a reservoir of fragrance is held, together with a wick to gradually evaporate the fragrance into the surrounding air. The reservoir is often defined within a cartridge that can be removed from the housing when exhausted and replaced. An example can be seen in our earlier application EP-A-2113259. These kinds of dispensers do however need to retain a quantity of fragrance, often in liquid form, which can be unpleasant if it escapes from the reservoir and is often an irritant. However, their long life between service intervals makes them attractive in commercial settings such as offices and washrooms.

Attempts to alleviate the problem have been through the use of viscous gels which are less likely to leak from a damaged reservoir than a fluid. However, the aromatic oils and emulsifiers used to ensure homogenous mixing of the oils in the aqueous solution often disrupt the gelling agents such that it is challenging to make a semi-solid gel with a high concentration of perfume. Furthermore, physical contact with the gel can result in the oil being released into the skin, potentially resulting in irritation.

An alternate fragrance delivery method is through the use of ceramic surface impregnated with a fragrance. The porous nature of ceramics enables them to readily take up a fragrance and then later release it into the environment. They have the advantage that the ceramic surface will not deposit significant amounts of oil onto surfaces touching them, so that they may be safely be picked up with bare hands.

SUMMARY OF THE INVENTION

In addition to the problems noted above, the use of a fragrance dispenser for an extended period will tend to lead to olfactory fatigue (also known as fragrance fatigue), i.e. a reduced ability to distinguish a fragrance after a prolonged exposure to that fragrance. An explanation of the mechanism of olfactory fatigue (or "olfactory adaptation") can be found at http://en.wikipedia.org/wiki/Olfactory fatigue.

The present invention attempts to address the problems with using the above methods to disperse fragrances. By using a dispenser comprising a ceramic outer shell impregnated with an evaporable liquid fragrance, and having an internal recess containing a fragranced gel, the gel fragrance being different to the liquid fragrance, which may as a whole be contained within a closed disposable container, this invention can solve the problems associated with touching a gel composition. Meanwhile, the amount of the more expensive ceramic needed to store the fragrance inside is minimised, and the longevity of the dispenser is increased markedly as it is not limited by the amount that can be absorbed by the ceramic.

The dispenser can comprise a generally cylindrical shell of greenware, a type of unfired ceramic. This is preferably impregnated with a fragrance, such as in the form of a volatile oil. The ceramic cylinder can have a closed end, which can be located at its lower end in order to retain the oil. It can also have an open end, ideally at the top, thus providing access to the interior. The fragranced gel composition can diffuse out of the gel and escape via the open end, from which it can be released into the air.

The result of this is to create a release system where fragrance can be released from the ceramic outer surface and from the gel composition. This allows for the fragrance release rate to remain consistently high (or at any particular level that is desired) over an extended period. In addition, the ceramic and the gel can be loaded with different fragrance compositions. As the release rate of a fragrance is dependent on the nature of the fragrance composition and the medium from which it is evaporating, these two fragrance compositions will typically release over a different period and at different rates. This will create a fragrance effect that varies over time, reducing the potential for olfactory fatigue.

To increase the versatility of the dispenser, the ceramic cartridge can have indentations to allow it to be retained in a desired location. We prefer that the indentations are used to permit the attachment of a plastic mounting clip. The plastic mounting clip can have a plurality of flexible arms that slot into the indentations to grip and hold the cartridge in place. This mounting clip could then be used to attach the cartridge to suitable surfaces such as a bathroom wall or the interior of a dispenser housing. Furthermore, the cartridge can have a locating recess on one or more of its sides, to receive a mounting post and thereby position the dispenser accurately and inhibit dislodgement.

An impermeable layer can be provided between the ceramic shell and the fragranced gel, to assist in preventing mixing of the two frangrances. The layer can be a plastics sleeve, or a latex layer, or the like.

The disposable container can comprise a receptacle and a lid, the two being engageable (such as via a screw-threaded interconnection) thereby to close the container. Other forms of container such as a frangible membrane are also possible.

The compounds that are released by a dispenser according to the present invention are not especially limited and may be any compounds or combination of compounds desired by the designer of the dispenser. As noted above, they may include compounds having aromatic properties, and/or odour-neutralising properties, and/or insect-repellent properties.

BRIEF DESCRIPTION OF THE DRAWINGS

An embodiment of the present invention will now be described by way of example, with reference to the accompanying figures in which;

FIG. 2 shows a side view of the fragrance dispenser cartridge of FIG. 1;

FIG. 3 shows a top view of the fragrance dispenser cartridge of FIG. 1;

FIG. 4 is a sectional view on A-A of FIG. 3;

FIG. 7 shows an exploded sectional view of a second embodiment;

FIG. 8 shows a perspective view of the assembled second embodiment; and

DETAILED DESCRIPTION OF THE EMBODIMENTS

Figure 1:
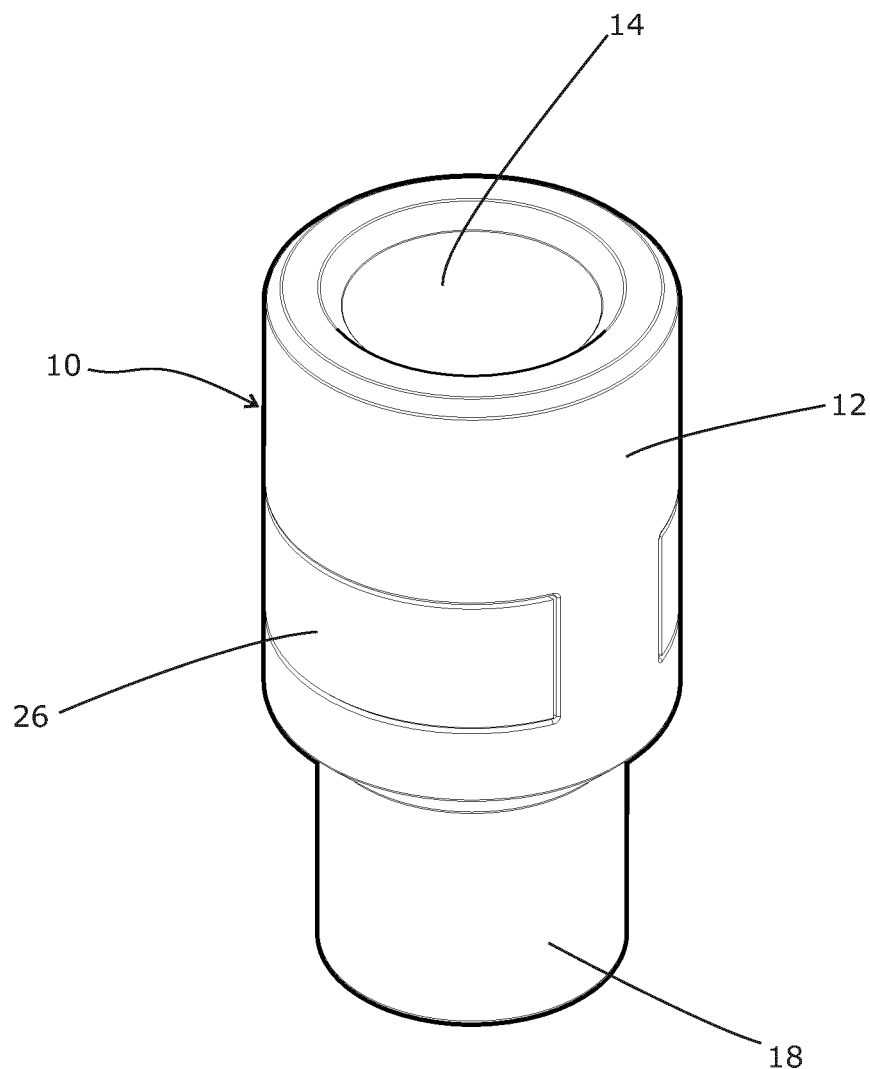
FIG. 1 shows an isometric view of a fragrance dispenser cartridge according to the present invention.

Referring to FIGS. 1 to 5, the fragrance cartridge 10 according to a first embodiment of the present invention comprises a ceramic outer shell 12 and a gel composition 14 contained within and retained by the outer shell 12. The embodiment is intended to provide a solid cartridge for use with dispensers such as that illustrated in FIG. 6. This is intended to alleviate problems relating to leakage and spillage, and avoid the need to "prime" the system (i.e. draw fluid from the cartridge into a dispensing mechanism).

The cartridge thus comprises a large moulded ceramic block impregnated with a fragrance complete with an integrated fragrance gel core working uniquely together in a timed release phase to provide consistent fragrance performance whilst overcoming fragrance fatigue issues. The product contains no liquid, so there is no chance of leaking in transit or use. It is classed as non-hazardous for all shipping methods. The external shape of the cartridge is intended to be a universal fit, i.e. one that fits into all existing dispensers.

The fragrance impregnated into the ceramic block is different to that provided in the gel core. This allows us to produce a multi fragrance product, with effects and characteristics that change substantially over time. These fragrances are designed such that the focus of the fragrance (the powerful key chemicals and notes) are significantly different. The diffusion rate of fragrance moving through ceramic is non-trivially different to that of fragrance evaporating from the surface of the gel. This allows us to design different mixtures to evaporate at different rates, so that one can be longer lasting than the other. These different mixtures (fragrances) can be chosen to be complementary, so that one fragrance ("a") in the gel and one fragrance ("b") in the ceramic, combine to produce a multitude of fragrances starting from primarily (a) or (b), developing over time to something in the middle being a balance of (a) & (b) and ending with either (b) and (a) [respectively]. Further, the fragrances for each part can be made of faster and slower evaporative chemicals (or groups of fragrance notes), such that each part (a) or (b) can have many sub-fragrances (a1, a2, a3, and b1, b2, b3) that interact with each other to form other final fragrances in the air. This type of product would be difficult to become accustomed to, and fragrance fatigue would be avoided.

The fragrance gel compounds that we prefer are generally composed of:

| Item | Amount (% amount by weight) |
| --- | --- |
| Carrageenan | 1.75 to 2.25 |
| Preservative | 0.15 |
| Polyethylene Glycol (PEG-400) | 15.0 to 20.0 |
| Fragrance | 10.0 to 25.0 |
| Polysorbate 20 | 5.0 to 10.0 |
| Water DI | 68.1 to 42.6 |
| Total | 100.00 |

Gels contain a carrier material, from which the perfume evaporates slowly and thus gives a pleasant smell to the atmosphere. The life time and the amount of perfume emitted per time unit are determined mainly by the amount of perfume in the air-freshener. In many known types of air-fresheners gelled water is used as carrier material. However, as perfumes are generally not or only hardly soluble in water, they should be dispersed therein as homogeneously as possible. Gelled organic solvents such as monohydric or polyhydric alcohols or glycol ethers can also be used as a carrier material, but water has the advantage of being cheap and toxicologically unsuspected.

Aqueous gels can be prepared in a wide range of known ways, using as a gelling agent compounds such as vegetable gums, especially carrageenan, agar-agar, alginates, pectin, guar gum, tragacanth, karaya gum and xanthan, or compounds such as gelatin, starch and cellulose derivatives. In some cases the gel strength can be increased by the addition of salts of bivalent or polyvalent metals like Ca, Mg, Al or Cr. Alternatively, synthetic polymers such as polyvinyl alcohol may be used as gelling agent. Such aqueous gels have the disadvantage that they may only contain a limited amount of perfume. In the literature a maximum perfume content of typically about 10% is mentioned, but in practice it appears that from a perfume content of more than about 6% strongly reduces the gel strength and/or causes syneresis whereby the perfume leaves the gel as a liquid. Aqueous perfume gels are described for instance in published Japanese patent applications 54/110,990 (gelling agent: carragheenin and sodium stearate, perfume content up to 6%); 53/088,334 (gelling agent: bacterial polysaccharide, 1-10% of perfume); and 52/136,893 (gelling agent: carragheenin and polyvinyl alcohol, 2-4% of perfume), and in French patent application 2,293,976 (gelling agent: carboxymethyl cellulose/Al-salt, 5% of perfume). Dutch patent application 76,11041 also discloses the use of carboxymethyl cellulose and salts of trivalent metals as gelling agent in aqueous perfume gels. Although it is mentioned in the specification that these gels may contain up to 20% of perfume, the examples only illustrate a perfume content of 4%. Likewise, Dutch patent application 76,02254 discloses similar aqueous perfume gels which are said to be capable of containing up to 10% of perfume, whereas in the examples only gels containing up to 23% of perfume are described. Dutch patent application 75,02596 describes aqueous gels based on mixtures of carragheenin and locust bean gum which according to the specification may also contain up to 10% of perfume, but from the examples it appears that no more than 3.3% of perfume is used. Dutch patent application 76,12909 discloses gels based on amylose as gelling agent; in the specification it is indicated that the perfume content of these gels is 0.25-30% preferably 0.5-5%. An example discloses a gel containing 30% of perfume, but for that result a content of 10% of pure amylose is required, with an attendant cost penalty. When starch containing 70% of amylose is used, no stable gel can be produced with even 10% of perfume. Furthermore these gels have the disadvantage that for the preparation of the necessary amylose-solution high temperatures (up to 170° C.) and pressures (up to 7 atm) are required, which therefore involves some relatively complicated equipment. In some of the above-mentioned patent applications, it is mentioned that the perfume is preferably used together with an amount of emulsifier for promoting the homogeneous distribution of the perfume in the aqueous phase. In Japanese patent application 52/070,035 it is stated that aqueous gels cannot contain more than 2-3% of perfume, except when a non-ionogenic emulsifier is added in an amount of 0.5-1.5 times the amount of perfume, in which case the perfume content of the gel may rise to 10%. The amount of perfume which can be distributed homogeneously in an aqueous gel highly depends on the solubility of the perfume in water and thus on the type of the composing components of the perfume.

The phrase "perfume" is used to mean a mixture of organic compounds such as aldehydes, ketones, nitriles, esters, carboxylic acids, alcohols and ethers which may also contain natural products like essential oils, resinoids, balsams and concretes. This mixture is meant to emit the desired smell. In many cases a perfume contains a mostly small amount of a solvent or diluent usual in perfumery, for instance because one or more of the components used in the composition are only available or manageable in solution.

Part of the water used for preparing the gel can optionally be replaced by water-miscible organic solvents like monohydric or polyhydric alcohols, for instance ethanol, isopropanol or ethylene glycol, as far as these solvents do not affect the good activity of the gelling agent used. This replacement is not generally recommended, but purely for economic reasons as organic solvents are more expensive than water.

The ceramic part can be constructed of any suitable adsorbent ceramic. We prefer on including 5 to 20% of Portland Cement Clinker together with the remaining 80 to 95% being made up of a plaster composition, ideally Calcium Sulphate hemihydrate, aka Plaster of Paris or Gypsum Plaster. These compound mixtures form a durable and stable greenware (i.e. an unfired ceramic) that is highly absorbent. It could optionally be fired in order to provide a harder surface without the loss of absorbency.

The Portland cement clinker is a mix of calcium silicates produced in the manufacture of Portland cement by sintering limestone and alumino-silicate (clay). For our purposes, it should consist of at least two-thirds by mass of calcium silicates (tricalcium silicate $3CaO.SiO_2$ and dicalcium silicate $2CaO.SiO_2$), the remainder consisting substantially of aluminium- and iron-containing clinker phases and other compounds. The ratio of CaO to $SiO_2$ should ideally not be less than 2.0. Any magnesium oxide content (MgO) should ideally not exceed 5.0% by mass. This compound can then be modified with Pozzolan type materials, if desired. Further details of the cement composition can be found at http://en.Wikipedia.org/wiki/Clinker (cement).

This compound can absorb essential oil, aromatics, hydrocarbons, deodorizing compounds and fragrance oils in amounts up to 150% of the ceramic's weight. The porosity is generally Low Hydrophobic or Lipophilic Conductivity.

The porosity & retentive qualities of the above "ceramic" type materials and blends allow the product to "hold" these fragrance compounds for extended periods of time, giving a time release quality and not allowing these compounds to leak and do damage. These slow release characteristics are particularly advantageous to the products longevity & functionality.

The actual physical construction of the "ceramic" cartridge is produced by hydrating the above blend of Plaster & Cement Clinker with water and casting it. The cast part is then allowed to "dry" or hydrate until the moisture content allows compounds of essential oils, aromatics, hydrocarbons, deodorizing compounds and fragrance oils to be absorbed without causing separation.

As can be seen in FIG. 4, the ceramic outer shell 12 is in a generally cylindrical form, with an internal closed bore 16 for receiving the gel composition 14. Thus, a base or lower portion 18 of the cylinder is closed, whereas an upper or top portion 20 of the cylinder is open. This means that the gel composition 14 is adequately supported, but also exposed to the atmosphere via the upper portion 20 thereby allowing it to evaporate. The bore 16 tapers so that near to the closed end 18 it is narrower in width than near to the open end 20; this aids insertion of the gel composition 14.

Figure 6:
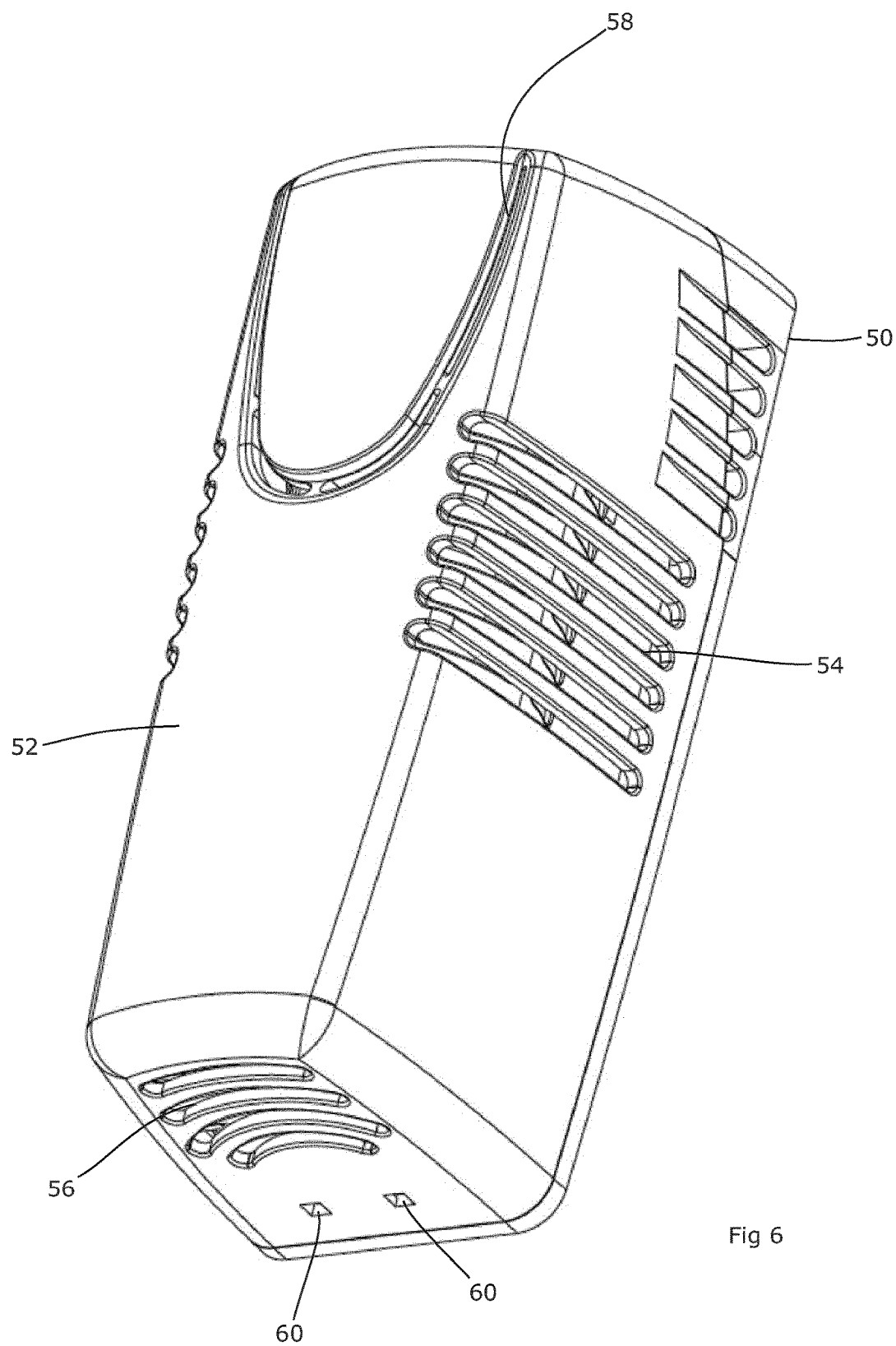
FIG. 6 shows a fragrance dispenser housing for containing the cartridge of FIGS. 1 to 5.

A recess 22 is provided on the external part of the base portion 18, for receiving a locating peg provided in certain dispensers (FIG. 6). This then holds the cartridge 10 in a secure manner.

Figure 5:
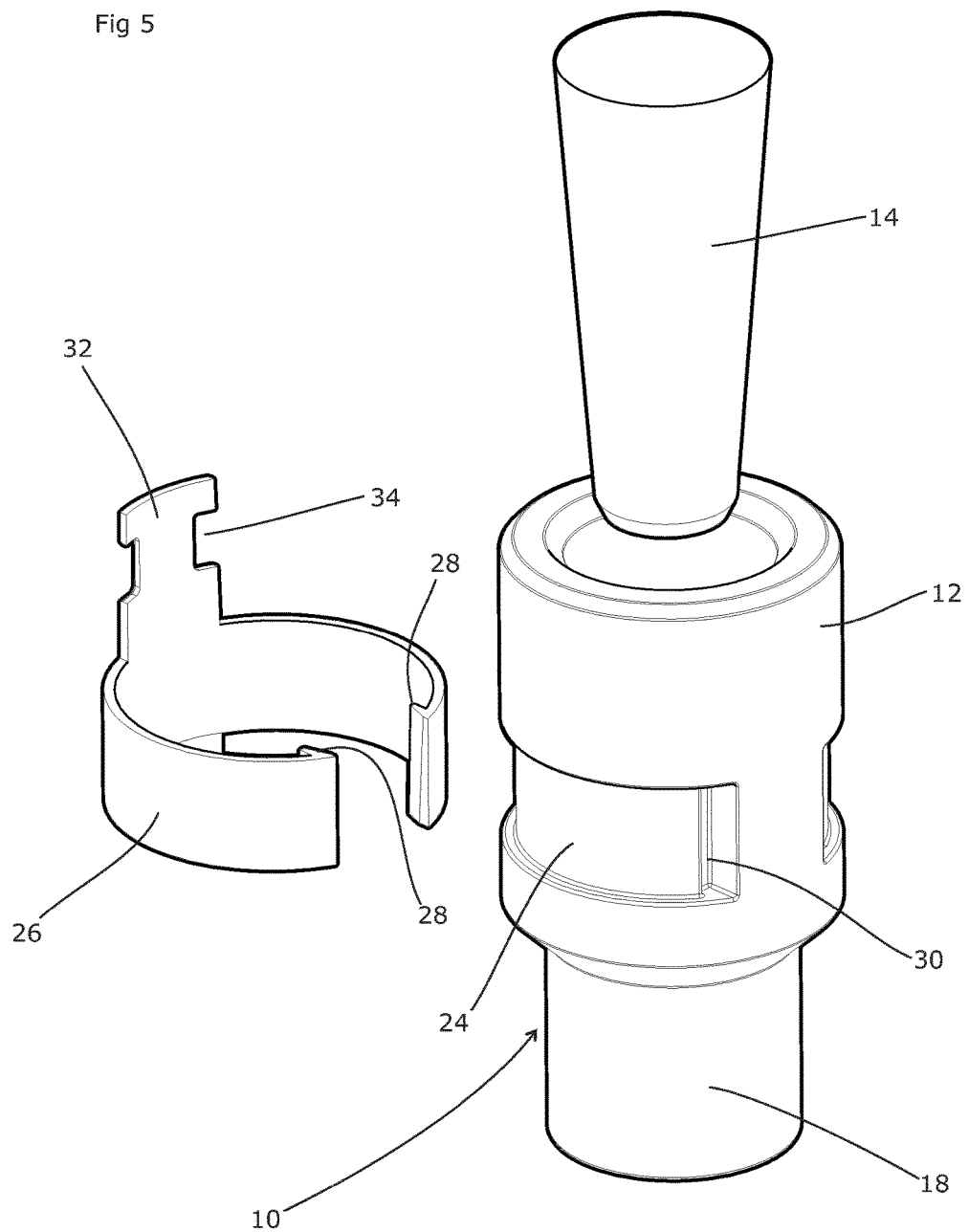
FIG. 5 is an exploded view of the fragrance dispenser cartridge of FIG. 1.

As can be seen most clearly in FIG. 5, the external sides of the ceramic shell 12 are formed with an indentation 24, defining a part-annular recess around the shell 12. This accepts a resilient plastics part-annular or C-shaped clip 26 that fits into the recess and holds the ceramic shell 12. At the ends of the part-annular clip 26, there are inwardly directed hooks 28 that engage with corresponding recesses 30 in the indentation 24, to allow the clip 26 to engage positively with the shell 12. The clip 26 also has a backplate 32 with engagement formations 34 to allow the clip to be attached to a dispenser housing, thereby supporting the cartridge 10 in place. The clip 26 may be one selected from a variety of clips, each having a backplate suited to one or more different types of dispenser, thus allowing the cartridge to fit any chosen design of dispenser.

FIG. 6 shows a typical dispenser housing. A detailed description is given in EP-A-2113259, to which the reader is referred for a fuller understanding and which is hereby incorporated by reference. This comprises a baseplate 50 and a cover 52 which is attached to the baseplate 50 via a hinge at their upper edges. Thus, the cover 52 may be lifted up on the hinge to reveal the interior of the housing. Formations on the baseplate 50 allow the baseplate 50 to be attached to a wall (or the like) via screws, bolts, or the like. A cartridge 10 can then be clipped to the baseplate 50 and the cover 52 closed to conceal the cartridge. Apertures on the sides (54), base (56) and front (58) faces of the cover 52 allow the fragrance emitted by the cartridge to escape into the room in which it is fitted. A lock mechanism prevents unauthorised opening of the cover 52, and is released by insertion of a special tool into apertures 60.

FIGS. 7 and 8 show a second embodiment of the present invention. The cartridge 100 once again comprises a ceramic outer shell 112 and a gel composition 114 within a recess 116 formed within the ceramic shell 112. In these and most respects this embodiment corresponds to the above-described embodiment of FIGS. 1 to 5. However, in addition, this embodiment comprises a liner 170 which sits between the gel composition 114 and the internal faces of the recess 116. The liner is of an impermeable material; various plastics materials such as polypropylene, polyethylene, polyvinylchloride, and the like, or materials such as latex, rubber, silicone and the like. This prevents mixing of the fragrances in the gel and in the ceramic, and assists in keeping the two fragrances distinct.

Figure 9:
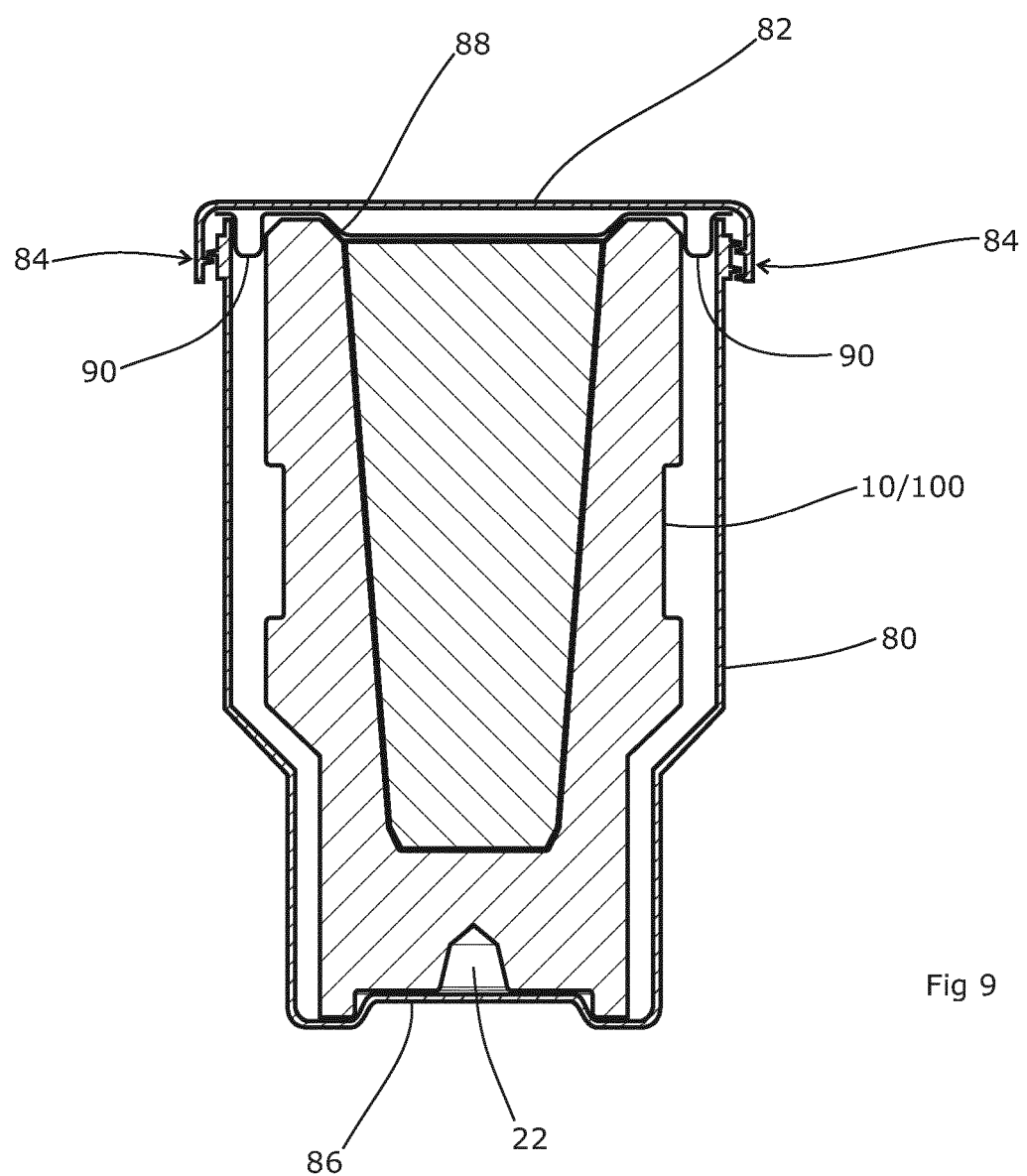
FIG. 9 shows a sectional view of the product as supplied within a container.

FIG. 9 shows the fragrance cartridge 10/100 as supplied ready for fitting within a dispenser housing. This cartridge may be according to the first or the second embodiment as desired. It sits within a receptacle 80 which has a cap 82 engaging via a screw-thread 84. The receptacle 80 is sized to fit around the cartridge 10/100 and has a bulge 86 on its base designed to engage with the recess 22 on the underside of the cartridge 10/100. This holds the lower part of the cartridge 10/100 in place, whilst the upper end is held in place by an inner lid 88 that fits on the top of the cartridge prior to fitting the cap 82. The inner lid 88 is generally conformal to the upper face of the cartridge 10/100 and has a resilient annular U-section ring 90 around the outside of the cartridge 10/100. This sits between the outer cylindrical face of the cartridge 10/100 and the inner cylindrical face of the receptacle 80, and thus braces the cartridge against movement, holding it in position. The inner lid 88 ends with a short lip that is sandwiched between the receptacle 80 and the cap 82, thus securing the inner lid 88 in place.

Thus packaged, the cartridge can be transported at will without risk to the ceramic shell. Minor bumps or knocks will be absorbed by the receptacle or the lid without causing damage to the cartridge. As the packaging is closed, evaporation of the fragrances will be inhibited. Other arrangements for packaging of the fragrance cartridge are possible, of course. For example, it could be enclosed within a frangible membrane such as a shrink-wrap plastics sleeve.

It will of course be understood that many variations may be made to the above-described embodiment without departing from the scope of the present invention.

The invention claimed is:

1. A fragrance dispenser comprising:
   a ceramic shell impregnated with an evaporable liquid fragrance, and having an internal recess containing a fragranced gel, the gel fragrance being different to the liquid fragrance, the ceramic shell having an opening for exposing the fragranced gel in the internal recess to the atmosphere without passing through the ceramic shell, the whole contained within a closed disposable container; and
   an impermeable layer located between the ceramic shell and the fragranced gel, the entire impermeable membrane remaining positioned between the ceramic shell and the fragranced gel when the fragranced gel is exposed to the atmosphere via the opening.

2. A fragrance dispenser according to claim 1 in which the ceramic shell is of greenware.

3. A fragrance dispenser according to claim 1 in which the ceramic shell is generally cylindrical.

4. A fragrance dispenser according to claim 3 in which the ceramic shell has a closed end.

5. A fragrance dispenser according to claim 4 in which the closed end is located at its lower end.

6. A fragrance dispenser according to claim 5 in which the opening is located at the top.

7. A fragrance dispenser according claim 1 in which the evaporable liquid fragrance is in the form of a volatile oil.

8. A fragrance dispenser according to claim 1 in which the evaporable liquid fragrance and the gel fragrance release over a different time period and/or at different rates.

9. A fragrance dispenser according to claim 1 in which the ceramic shell has indentations on an exterior surface thereof.

10. A fragrance dispenser according to claim 9 further comprising a mounting clip shaped to engage with the indentations.

11. A fragrance dispenser according to claim 10 in which the mounting clip is of a plastics material.

12. A fragrance dispenser according to claim 10 in which the mounting clip comprises a plurality of flexible arms that are engageable with the indentations.

13. A fragrance dispenser according to claim 1 further comprising a dispenser housing, within which the ceramic outer shell is locatable.

14. A fragrance dispenser according to claim 13 in which one of the ceramic shell and the dispenser housing has a locating recess, and the other has a mounting post engageable within the locating recess thereby to position the ceramic shell within the dispenser housing.

15. A fragrance dispenser according to claim 1, in which the impermeable layer is a plastics sleeve.

16. A fragrance dispenser according to claim 1, in which the impermeable layer is a latex layer.

17. A fragrance dispenser according to claim 1 in which the disposable container comprises a receptacle and a lid, the two being engageable thereby to close the container.

18. A fragrance dispenser according to claim 17 in which the receptacle and the lid are engageable via a screw-threaded interconnection.

19. A fragrance dispenser according to claim 1 in which the disposable container comprises a frangible membrane.

\* \* \* \* \*